United States Patent [19]

Atkinson et al.

[11] Patent Number: 5,221,678

[45] Date of Patent: Jun. 22, 1993

[54] (QUINOLIN-2-YLMETHOXY)TETRAHYDROCARBAZOLES AS INHIBITORS OF THE BIOSYNTHESIS OF LEUKOTRIENES

[75] Inventors: Joseph G. Atkinson, Montreal; John W. Gillard; Erich L. Grimm, both of Baie d'Urfe, all of Canada

[73] Assignee: Merck Frosst Canada, Inc., Kirkland, Canada

[21] Appl. No.: 729,017

[22] Filed: Jul. 12, 1991

Related U.S. Application Data

[63] Continuation-in-part of Ser. No. 558,971, Jul. 26, 1990, abandoned.

[51] Int. Cl.[5] .................. C07C 215/12; C07C 215/04; A01N 43/42
[52] U.S. Cl. ..................................... 514/311; 514/312; 514/313; 514/314; 546/153; 546/155; 546/156; 546/167; 546/168; 546/169; 546/170; 546/171; 546/172; 546/174; 546/175; 546/176
[58] Field of Search ............... 546/172, 174, 153, 155, 546/156, 167, 168, 169, 170, 171, 175, 176; 514/311, 312, 313, 314

[56] References Cited

U.S. PATENT DOCUMENTS

| | | | |
|---|---|---|---|
| 4,057,559 | 11/1977 | Asselin et al. | 548/439 |
| 4,578,398 | 3/1986 | Mobilio et al. | 514/411 |
| 4,808,608 | 2/1989 | Guindon et al. | 514/411 |
| 4,920,132 | 4/1990 | Huang et al. | 514/314 |
| 4,929,626 | 5/1990 | Mohrs et al. | 514/311 |
| 4,962,203 | 10/1990 | Young et al. | 546/180 |
| 4,970,215 | 11/1990 | Mohrs et al. | 514/311 |

FOREIGN PATENT DOCUMENTS

| | | |
|---|---|---|
| 0339416 | 11/1989 | European Pat. Off. . |
| 0344519 | 12/1989 | European Pat. Off. . |
| 349062 | 1/1990 | European Pat. Off. . |
| WO91/06537 | 5/1991 | PCT Int'l Appl. . |
| 1382513 | 2/1975 | United Kingdom . |

Primary Examiner—C. Warren Ivy
Assistant Examiner—Raymond Covington
Attorney, Agent, or Firm—Gabriel Lopez; Joseph F. DiPrima

[57] ABSTRACT

Compounds having the Formula I:

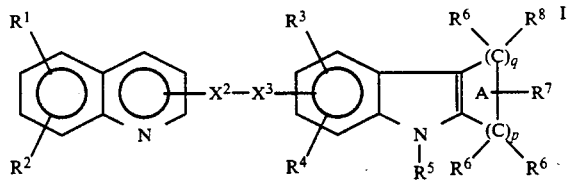

are inhibitors of leukotriene biosynthesis. These compounds are useful as anti-asthmatic, anti-allergic, anti-inflammatory, and cytoprotective agents. They are also useful in treating diarrhea, hypertension, angina, platelet aggregation, cerebral spasm, premature labor, spontaneous abortion, dysmenorrhea, and migraine.

9 Claims, No Drawings

(QUINOLIN-2-YLMETHOXY)TETRAHYDROCARBAZOLES AS INHIBITORS OF THE BIOSYNTHESIS OF LEUKOTRIENES

CROSS-REFERENCE

This is a continuation-in-part of U.S. Ser. No. 558,971, Jul. 26, 1990, now abandoned.

BACKGROUND OF THE INVENTION

The leukotrienes and their biological activities, especially their roles in various disease states and conditions have been described. For example, see U.S. Pat. No. 4,683,325 (Jul. 28, 1987), which is incorporated herein by reference.

Several classes of compounds exhibit the ability to inhibit the biosynthesis of leukotrienes in mammals, especially humans. For example, EP 349,062 (Merck) describes a series of compounds of the general formula A:

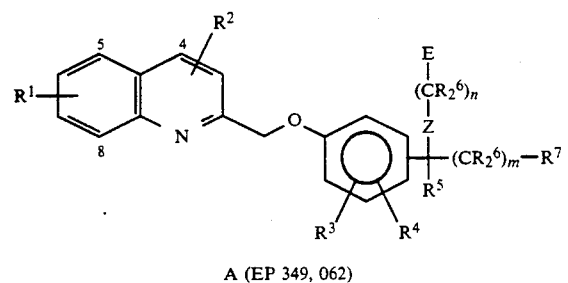

A (EP 349, 062)

EP 339,416 (Bayer) and 344, 519 (Bayer) describe compounds of Formulas B and C respectively:

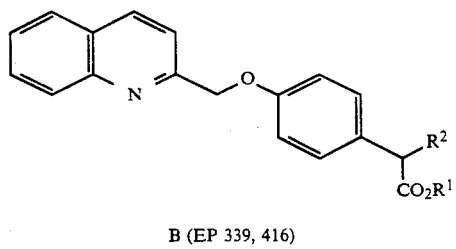

B (EP 339, 416)

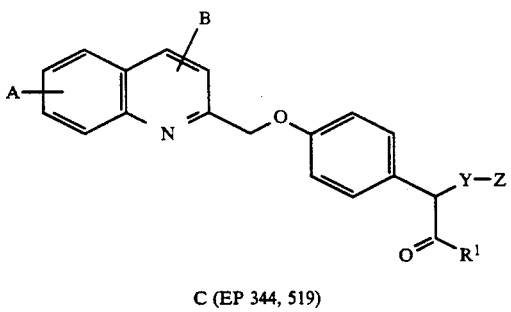

C (EP 344, 519)

The above compounds differ chemically from the present invention in a major structural feature. Namely, the compounds of the present invention contain a tetrahydrocarbazole nucleus, which is absent from the above.

Compounds D, E, F and G, containing tetrahydrocarbazole structures, are described in U.S. Pat. Nos. 4,578,398 (AHP), 4,057,559 (AHP), and 4,808,608 (Merck), and U.K. 1,382,513 (Roche) as having various biological activities. However, none of these compounds contain a quinoline nucleus joined to the tetrahydrocarbazole moiety, and such a major change would not obviously give rise to any particularly useful biological activity.

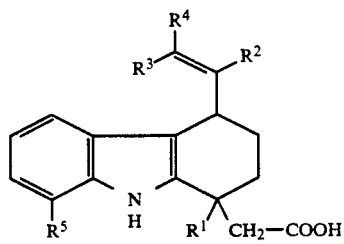

D (U. S. Pat. No. 4,578,398)

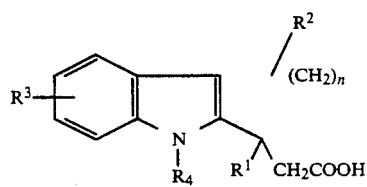

E (U. S. Pat. No. 4,057,559)

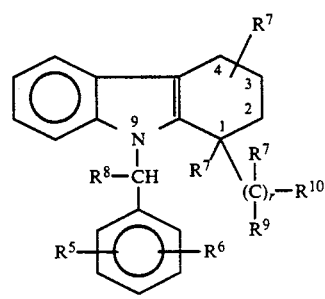

F (U. S. Pat. No. 4,808,608)

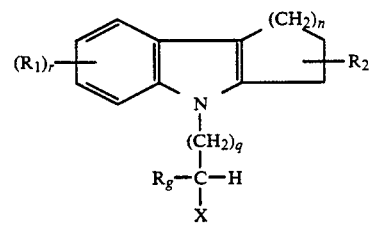

G (G.B. 1,382,513)

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to inhibit the pathologic actions of leukotrienes on the cardiovascular and vascular systems for example, actions such as result in angina or endotoxin shock. The compounds of the present invention are useful in the treatment of inflammatory and allergic diseases of the eye, including allergic conjunctivitis. The compounds are also useful as cytoprotective agents and for the treatment of migraine headache.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are inhibitors of the biosynthesis of 5-lipoxygenase metabolites of arachidonic acid, such as 5-HPETE, 5-HETE and the leukotrienes. Leukotrienes $B_4$, $C_4$, $D_4$, and $E_4$ are known to contribute to various disease conditions such as asthma, psoriasis, pain, ulcers and systemic anaphylaxis. Thus, inhibition of the synthesis of such compounds will alleviate these and other leukotriene-related disease states.

DETAILED DESCRIPTION OF THE INVENTION

The present invention provides novel compounds of Formula I:

wherein:
each of $R^1$, $R^2$, $R^3$, $R^4$ and $R^{10}$ is independently hydrogen, halogen, lower alkyl, lower alkenyl, lower alkynyl, $-CF_3$, $-CN$, $-NO_2$, $-N_3$, $-C(OH)R^6R^6$, $-C(O)OR^{12}$, $-SR^{13}$, $-S(O)R^{13}$, $-S(O)_2R^{13}$, $-S(O)_2NR^{15}R^{15}$, $-C(O)NR^{15}R^{15}$, $-OR^{15}$, $-NR^{15}R^{15}$, $-C(O)R^{16}$ or $-(CH_2)_rR^{21}$;
$R^5$ is hydrogen or $X-R^9$;
$R^6$ is independently hydrogen or lower alkyl, or two $R^6$ groups on the same carbon atom are joined to form a cycloalkyl ring of 3 to 6 carbon atoms;
$R^7$ is $-(CR^6R^6)_sQ$;
$R^8$ is hydrogen, $R^9$, $-CR^{23}=CR^{24}R^{25}$, $-C(Cl)=CCl_2$ or $R^6$ plus $R^8$ on the same carbon atom may be a double bonded oxygen (=O);
$R^9$ is alkyl, alkenyl, $-(CH_2)_tPh(R^{10})_2$ or $-(CH_2)_tTh(R^{10})_2$;
$R^{11}$ is the structure of a standard amino acid except for the amino group α to the carboxy group, or $R^{11}$ and $R^{18}$ attached to the same nitrogen can cyclize to form a proline residue;
$R^{12}$ is hydrogen, lower alkyl or $-CH_2R^{21}$;
$R^{13}$ is $-CF_3$ or $R^{14}$;
$R^{14}$ is lower alkyl or $-(CH_2)_uR^{21}$;
$R^{15}$ is hydrogen, $-C(O)R^{16}$, $R^{14}$, or two $R^{15}$ groups on the same nitrogen may be joined to form a heterocyclic ring of 4 to 6 atoms containing up to 2 heteroatoms chosen from O, S or N;
$R^{16}$ is hydrogen, lower alkenyl, lower alkynyl, or $R^{13}$;
$R^{17}$ is $-(CH_2)_v-C(R^{18}R^{18})-(CH_2)_v-R^{19}$ or $-CH_2-C(O)NR^{15}R^{15}$;
$R^{18}$ is hydrogen or lower alkyl;
$R^{19}$ is
   a) a monocyclic or bicyclic heterocyclic radical containing from 3 to 9 nuclear carbon atoms and 1 or 2 nuclear hetero-atoms selected from N, S or O and with each ring in the heterocyclic radical being formed of 5 or 6 atoms, or
   b) the radical $W-R^{20}$;
$R^{20}$ contains up to 21 carbon atoms and is (1) a hydrocarbon radical or (2) an acyl radical of an organic acyclic or monocyclic carboxylic acid containing not more than 1 heteroatom in the ring;
$R^{21}$ is phenyl substituted with 1 or 2 $R^{22}$ groups;
$R^{22}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;
$R^{23}$ is $R^{18}$ or $R^{23}$ and $R^{24}$ may form a bond;
$R^{24}$ is $R^6$ or $R^{23}$ and $R^{24}$ may form a bond;
$R^{25}$ is $R^6$;
p is 2 to 5;
q is 0 or 1;
p+q is 3 to 5;
r is 0 to 2;
s is 0 to 4;
t is 0 to 3;
u is 0 to 3;
v is 0 to 3;
W is O, S or $NR^{15}$;
X is C(O), $CR^6R^6$, $S(O)_2$ or a bond;
$X^2-X^3$ is $CH_2O$, $CH_2S$, $CH_2S(O)_2$, $CH_2CH_2$, or $CH=CH$;
Q is $-C(O)NR^{11}R^{18}$ $-C(O)OR^{12}$, $-C(O)NH-S(O)_2R^{13}$, $-NHS(O)_2R^{13}$, $-S(O)_2NHR^{15}$, $-C(O)NR^{15}R^{15}$, $-C(O)OR^{17}$, $-CH_2OH$, or 1H- or 2H-tetrazol-5-yl;
or the pharmaceutically acceptable salts thereof.

A preferred embodiment of Formula I is that in which:
each of $R^1$, $R^2$, $R^3$ and $R^4$ is hydrogen;
$R^5$ is $X-R^9$;
$R^8$ is $R^9$;
$R^{10}$ is hydrogen or halogen;
the $CH_2O$ is attached to the 2-position of the quinoline ring;
p+q is 4;
X is a bond;
$X^2-X^3$ is $CH_2O$;
Q is $-C(O)OR^{12}$;
and the remaining substituents are as defined for Formula I; or the pharmaceutically acceptable salts thereof.

Definitions

The following abbreviations have the indicated meanings:
Ac=acetyl
$C_3H_5$=allyl
Bz=benzyl
c-=cyclo
c-$C_6H_{11}$=cyclohexyl
c-Pr=cyclopropyl
Et=ethyl
i-Pr=isopropyl
Me=methyl Ph=phenyl
t-Bu=tert-butyl
Tz=5-tetrazolyl
Th=2- or 3-thienyl.

Alkyl, alkenyl, and alkynyl are intended to include linear, branched, and cyclic structures and combinations thereof.

The term "alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

The term "lower alkyl" includes those alkyl groups of from 1 to 7 carbon atoms. Examples of lower alkyl groups include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

The term "alkenyl" includes "lower alkenyl" and extends to cover carbon fragments having up to 20 carbon atoms. Examples of alkenyl include oct-2-en-1-yl, 3-(cyclohexen-1-yl)propyl, octadec-9-en-2-yl and the like.

"Lower alkenyl" groups include those alkenyl groups of 2 to 7 carbon atoms. Examples of lower alkyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, and the like.

The term "alkynyl" includes "lower alkynyl" and extends to cover carbon fragments having up to 20 carbon atoms. The acetylene group may be included within a ring structure of 10 members or more. Examples of alkynyl include dodec-2-yn-1-yl, 1-cyclohexyl-but-1-yn-4-yl, cyclohexadecyn-3-yl, and the like.

"Lower alkynyl" groups include those alkynyl groups of 2 to 7 carbon atoms. Examples of lower alkynyl groups include ethynyl, propargyl, 3-methyl-1-pentynyl, 2-heptynyl, and the like.

The term "lower alkoxy" includes those alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

The term "lower alkylthio" includes those alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

The term "lower alkylsulfonyl" includes those alkylsulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, etc. By way of illustration the 2-butylsulfonyl group signifies —$S(O)_2CH(CH_3)CH_2CH_3$.

The term "lower alkylcarbonyl" includes those alkylcarbonyl groups of from 1 to 8 carbon atoms of a straight, branched or cyclic configuration. Examples of lower alkylcarbonyl groups are formyl, 2-methylbutanoyl, cyclohexylacetyl, etc. By way of illustration, the 2-methylbutanoyl group signifies —$C(O)CH(CH_3)CH_2CH_3$.

The terms $Ph(R^{10})_2$ and $Th(R^{10})_2$ indicate a phenyl or thienyl group substituted with two $R^{10}$ substituents.

Halogen means F, Cl, Br, and I.

It is intended that the definitions of any substituent (e.g., $R^1$, $R^2$, $Ph(R^{10})_2$ etc.) in a particular molecule be independent of its definitions elsewhere in the molecule. Thus, —$NR^{15}R^{15}$ represents —NHH, —$NHCH_3$, —$NHC_6H_5$, etc.

The heterocycles formed when two $R^{15}$ groups join through N are pyrrolidine, piperidine, morpholine, thiamorpholine, piperazine, and N-methylpiperazine.

The prodrug esters of Q (i.e., when Q=$CO_2R^{17}$) are intended to include the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3, 451–454 (1987).

Within the definition of $R^{19}$, some representative monocyclic or bicyclic heterocyclic radicals are:
2,5-dioxo-1-pyrrolidinyl,
(3-pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

The term standard amino acid is employed to include the following amino acids: alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine. (See F. H. C. Crick, Symposium of the Society of Experimental Biology, 1958 (12), p. 140).

It is understood that $R^1$ and $R^2$ may be located at any unoccupied positions of the quinoline ring. The group $R^7$ replaces one of the $R^6$ groups attached to the carbons which make up ring A.

Optical Isomers and Diastereomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N¹-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for inhibiting the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary conditions including diseases such as asthma, 2) allergies and allergic reactions such as allergic rhinitis, contact dermatitis, allergic conjunctivitis, and the like, 3) inflammation such as arthritis or inflammatory bowel disease, 4) pain, 5) skin conditions such as psoriasis and the like, 6) cardiovascular conditions such as angina, endotoxin shock, and the like and 7) renal insufficiency arising from ischaemia induced by immunological or chemical (cyclosporin) etiology and that the compounds are cytoprotective agents.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations with other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

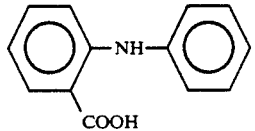

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

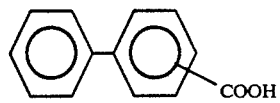

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

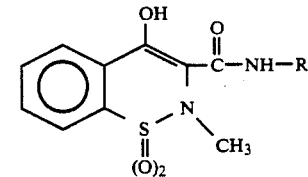

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP 56,172 (Jul. 21, 1982) and 61,800 (Jun. 10, 1982); and in U.K. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^{30}$ /$H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in U.K. Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following Schemes. Temperatures are in degrees Celsius.

SCHEME 1

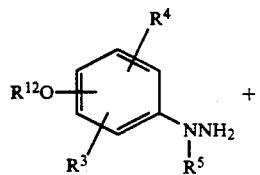

1

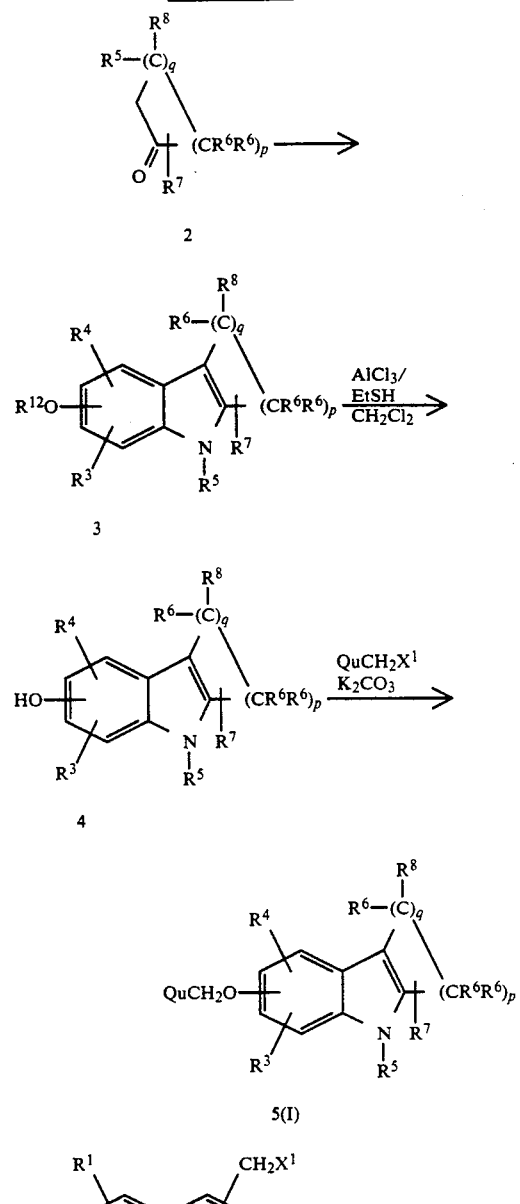

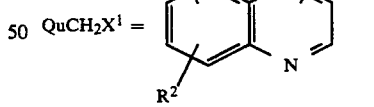

Scheme 1

The starting oxygenated phenylhydrazines 1 are either commercially available or are described in the chemical literature. Thus EP 166,591 describes the preparation of 1 when $R^5$ is a substituted benzyl group. B. Robinson lists a number of phenylhydrazine derivatives of structure 1 in his book The Fischer Indole Synthesis, John Wiley & Sons, Toronto, pp. 557-591 (1982).

Many ketones 2 are described in the chemical literature and many can be readily prepared by standard modifications of known procedures.

The halomethyl quinolines $QuCH_2X^1$ ($X^1$ is Cl, Br or I) are available from literature methods described in

*Quinolines*, Parts I and II, G. Jones, Ed., John Wiley & Sons, Toronto (1977 and 1982). The preparation of QuCH₂X¹ by halogenation of the corresponding methyl quinolines is also described in the Jones volumes.

The phenylhydrazine 1 is made to undergo a Fischer indole reaction with ketone 2 in a suitable solvent such as acetic acid or formic acid. Alternatively, the hydrochloride salt of 1 will undergo the Fischer reaction with 2 in neutral solvents such as dimethylformamide, (DMF), ethanol, t-butanol, dioxane, etc., or in acetic acid. For further indications on the Fischer indole synthesis, see the above-mentioned book by B. Robinson or *Heterocyclic Compounds*, Volume 25, Parts I, II, III, W. J. Houlihan, Ed., Interscience, J. Wiley & Sons, New York, 1979. If $R^{12}$ of 1 is hydrogen, this reaction furnishes compound 4 directly. Compound 4 is prepared from 3 by de-alkylation (or de-benzylation when $R^{12}$ is a benzyl group) using an aluminum, gallium or boron halide in conjunction with an alkyl mercaptan in a neutral solvent such as benzene, $CH_2Cl_2$, $CH_2ClCH_2Cl$, etc. Phenol 4 is then coupled to the halomethylquinoline, QuCH₂X¹ by stirring the two together in a suitable solvent such as DMF, acetone, or N-methyl pyrrolidone (NMP), etc., in the presence of a base such as $K_2CO_3$, $KHCO_3$, $Na_2CO_3$ or $Cs_2CO_3$, etc. Product 5 is an example of the compound of the present invention. Compound 5 ($R^5 = H$) can be reacted with various electrophiles, using potassium hexamethyldisilazide as base, and $R^5—X^1$ as electrophiles ($R^5$ not=H) to yield the N-substituted compounds 5 ($R^5$ not=H). If desired, Q in $R^7$ of 5 can be hydrolyzed to the corresponding carboxylic acid by standard procedures known in the art.

Scheme 2

A suitable N-acetylated aminophenol 6 is reacted with QuCH₂X¹ using an alkali hydride or carbonate, such as potassium carbonate as a base in a polar solvent like DMF or NMP. The quinolinylmethoxy acetanilide 7 is then de-acetylated using standard basic conditions, preferably using alcoholic potassium hydroxide under reflux to produce the quinolinylmethoxy aniline derivative 8. Conversion of the quinolinylmethoxy aniline derivative to the hydrazine analogue 9 is effected through reduction of the intermediate diazonium salt using sodium hydrosulfite in an aqueous medium.

The hydrazine 9 is then N-benzylated using a benzyl halide in an organic solvent such as methylene chloride containing an amine base such as diisopropylethylamine and preferably tetra-n-butylammonium bromide as catalyst.

The hydrazine 10 is then processed using a Fischer indolization with ketone 2 according to Scheme 1 to produce compounds 5 of the present invention.

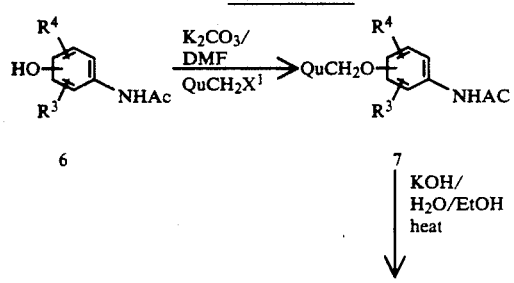

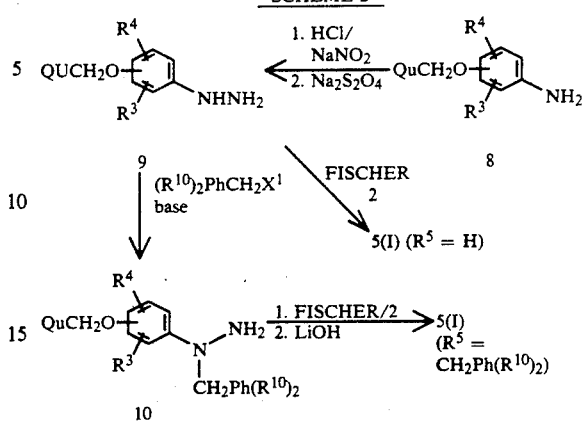

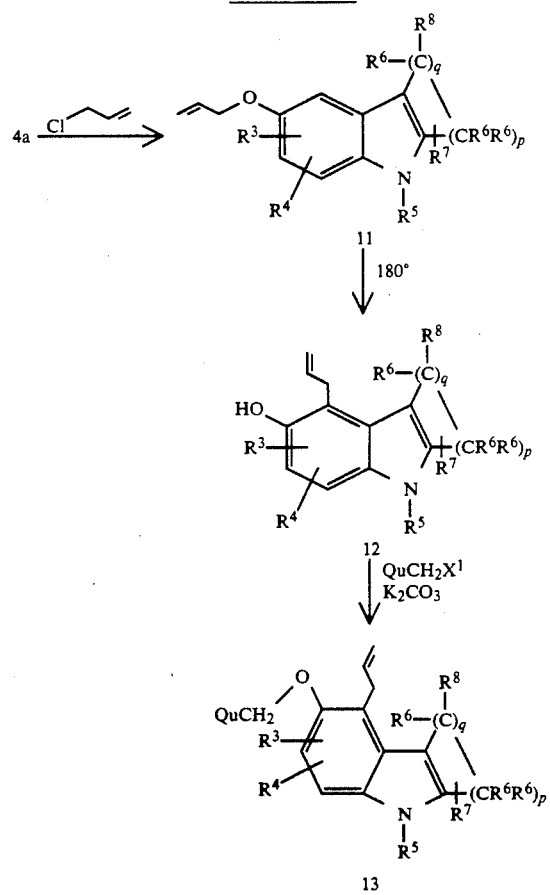

Scheme 3

Scheme 3 illustrates the introduction of an allyl group into compounds of the present invention. The method indicated through the intermediates 11 and 12 is known as the Claisen rearrangement, and is well in the art: S. J. Rhoads and N. R. Raulins, *The Claisen and Cope Rearrangements*, in *Organic Reactions*, Vol. 22, pp. 1–252 (1975). The allyl group can in turn be converted into many other functionalities by standard procedures of organic chemistry (e.g. hydroboration, reduction, epoxidation, oxidative cleavage, etc.).

SCHEME 4

HO—THC* —Me₂NCSCl→ Me₂NCS—O—THC
4                         14
(SCHEME 1)
                          | heat
                          ↓

HS—THC ←MeONa/MeOH— Me₂NCO—S—THC
16                        15

| QuCH₂X¹
| Base
↓

QuCH₂S—THC —H₂O₂/HOAc→ QuCH₂S(O)₂—THC
17  (I)                    17a  (I)

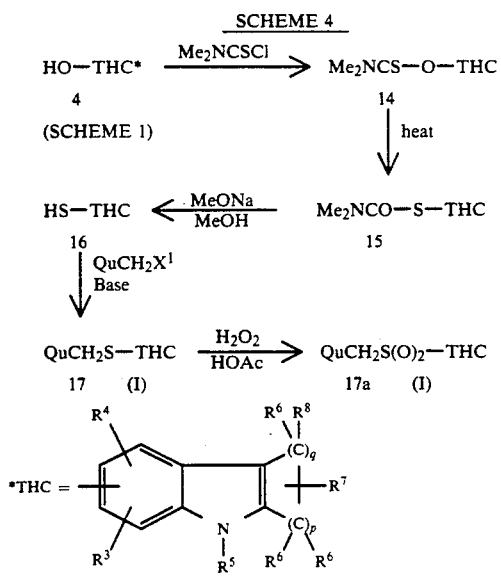

Scheme 4

In Scheme 4 the routes used to prepare compounds of formula I where $X^2—X^3 = —CH_2S—$ are described. As the first step, the phenolic indole 4 (from Scheme 1) is dissolved in an organic solvent (e.g., DMF) and is treated with an inorganic base such as NaH followed by the addition of dimethylthiocarbamoyl chloride to provide the intermediate 14. Heating the intermediate 14 neat causes the compound to rearrange to give the thiophenol derivative 15. This compound when refluxed in a solution of, for example, sodium methoxide in methanol and then, if necessary, reduction of the disulfide bond (triphenylphosphine, 6N HCl in an organic solvent such as dioxane) gives the thiophenol 16. The thiol group of intermediate 16 may be alkylated by stirring a solution of the thiophenol 16, a base such as $K_2CO_3$ or triethylamine and an appropriate alkylating agent, QuCH₂X¹ in a solvent such as THF. This procedure affords the product 17 which is an example of compound I of the present invention.

Oxidation of 17 with two equivalents of a mild oxidizing agent such as hydrogen peroxide in acetic acid or meta-chloroperbenzoic acid in methylene chloride yields the corresponding sulfone 17a.

SCHEME 5

HO—THC —Tf₂O/C₂H₅N→ TfO—THC
4                         18
(Scheme 1)
                          | CO,
                          | DPE,
                          | Pd(OAc)₂
                          ↓

HOCH₂—THC ←LiBH₄— MeO₂C—THC
20                        19

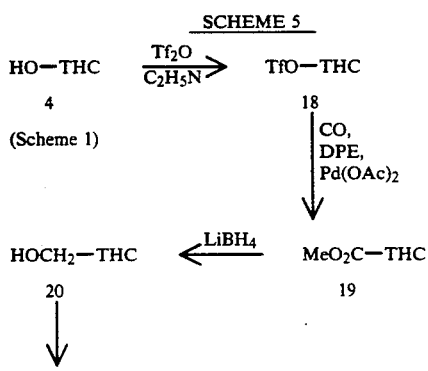

-continued
SCHEME 5

OHC—THC —QuCH₂P(Ph)₃X¹/BuLi→ Qu—CH=CH—THC
21                              22  (I)
                                | H₂
                                | Pd/C
                                ↓

Qu—CH₂CH₂—THC
                                23  (I)

Scheme 5

Compounds corresponding to Formula I where $X^2X^3 = —CH=CH—$ or $—(CH_2)_2—$ are prepared as in Scheme 5. Phenol 4 (from Scheme 1) may be converted to triflate 18 by stirring with trifluoromethanesulfonic anhydride (Tf₂O) and an organic base (e.g., pyridine) in a solvent such as dichloromethane. A solution of triflate 18 in DMSO/methanol with an organic base such as triethylamine, a phosphine such as diphenylphosphinoethane (DPE), a palladium II salt (e.g., palladium(II) acetate) and an atmosphere of carbon monoxide gives the ester 19. Reaction of 19 with a reducing agent, for example lithium borohydride, in an organic solvent such as THF yields the alcohol 20.

Alcohol 20 may be oxidised using, for example, manganese dioxide in an organic solvent such as dichloromethane to produce aldehyde 21. A Wittig reaction between aldehyde 21 and an ylid derived from deprotonation of a phosphonium salt, QuCH₂P(Ph)₃X¹, using an inorganic base (e.g., n-BuLi) in an organic solvent such as THF affords the unsaturated product 22 (I). Compound 22 may be hydrogenated in an alcoholic solvent (e.g., methanol) using a catalyst such as 10% palladium on carbon and a hydrogen atmosphere to yield the saturated compound 23.

If desired, Q in $R^7$ in compounds 17, 22, or 23 can be hydrolyzed to the corresponding carboxylic acid by standard procedures known in the art.

SCHEME 6

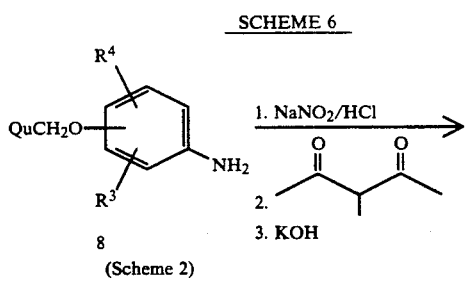

(Scheme 2)

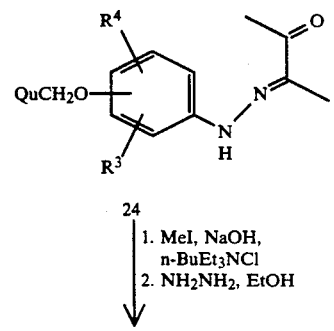

24
1. MeI, NaOH,
   n-BuEt₃NCl
2. NH₂NH₂, EtOH
↓

-continued
SCHEME 6

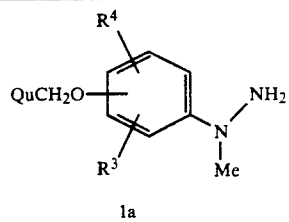

1a table, the left hand carbon of the unit $(CR^6R^6)_p$ is attached to position-2 of the indole ring and the right hand carbon to the unit $(R^6CR^8)_q$.

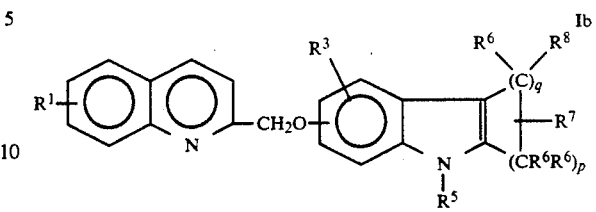

Ib

Scheme 6

TABLE I

| Ex | Attach point | $R^1$ | $R^3$ | $R^5$ | $R^7$ | $(CR^6R^6)_p$ | $(R^6CR^8)_q$ |
|---|---|---|---|---|---|---|---|
| 1 | 6 | H | H | p-ClBz | 1-CH$_2$CO$_2$H | (CH$_2$)$_3$ | HCH |
| 2 | 6 | H | H | p-ClBz | 2-CH$_2$CO$_2$H | (CH$_2$)$_3$ | HCH |
| 3 | 6 | H | H | p-ClBz | 2-CO$_2$H | (CH$_2$)$_3$ | HCH |
| 4 | 6 | H | H | p-ClBz | 1-CO$_2$H | (CH$_2$)$_3$ | HCH |
| 5 | 6 | H | H | p-ClBz | 3-CO$_2$H | (CH$_2$)$_3$ | HCH |
| 6 | 6 | H | H | p-ClBz | 1-(CH$_2$)$_2$CO$_2$H | (CH$_2$)$_3$ | HCH |
| 7 | 6 | 7-Cl | H | p-ClBz | 1-CH$_2$CO$_2$H | (CH$_2$)$_3$ | HCH |
| 8 | 6 | H | H | p-ClPhCO | 1-CH$_2$CO$_2$H | (CH$_2$)$_3$ | HCH |
| 9 | 6 | H | 5-C$_3$H$_5$ | p-ClBz | 1-CH$_2$CO$_2$H | (CH$_2$)$_3$ | HCH |
| 10 | 6 | H | H | p-ClBz | 1-CH$_2$CO$_2$H | (CH$_2$)$_3$ | HCPH |
| 11 | 7 | H | H | Me | 1-CH$_2$CO$_2$H | (CH$_2$)$_3$ | HCPh |
| 12 | 7 | H | H | Me | 1-CH$_2$CO$_2$H | (CH$_2$)$_3$ | MeC-p-ClPh |
| 13 | 7 | H | H | COMe | 1-CH$_2$CO$_2$H | (CH$_2$)$_3$ | HC-p-ClPh |
| 14 | 2 | H | H | p-ClBz | 6-CH$_2$CO$_2$H | (CH$_2$)$_4$ | HC-p-ClPh |
| 15 | 2 | H | H | p-ClBz | 7-CH$_2$CO$_2$H | (CH$_2$)$_4$ | HC-p-ClPh |
| 16 | 2 | H | H | p-ClBz | 7-CO$_2$H | (CH$_2$)$_4$ | HCH |
| 17 | 3 | H | H | Me | 6-CH$_2$CO$_2$H | (CH$_2$)$_4$ | HC-p-ClPh |
| 18 | 3 | H | H | Me | 7-CO$_2$H | (CH$_2$)$_4$ | HC-p-ClPh |
| 19 | 3 | H | H | Me | 7-CONH$_2$ | (CH$_2$)$_4$ | HC-p-ClPh |
| 20 | 6 | H | H | p-ClBz | 1-CH$_2$CO$_2$H | CH$_2$CH$_2$CH(t-Bu) | HCH |
| 21 | 6 | H | 5-Me | p-MeS(O)$_2$Bz | 1-CH$_2$CO$_2$H | (CH$_2$)$_3$ | C=O |
| 22 | 6 | H | H | p-ClBz | 1-CH$_2$CO$_2$H | CH$_2$CH(t-Bu)CH$_2$ | C=O |
| 23 | 5 | H | H | p-ClBz | 1-CH$_2$CO$_2$H | (CH$_2$)$_3$ | HCH |
| 24 | 6 | H | H | Bz | 1-CH$_2$CO$_2$H | (CH$_2$)$_3$ | HCH |
| 25 | 7 | H | H | p-ClBz | 3-CH$_2$CO$_2$H | (CH$_2$)$_2$ | HCH |
| 26 | 6 | H | H | Me | 3-CH$_2$CO$_2$H | (CH$_2$)$_2$ | HCPh |
| 27 | 6 | H | H | p-ClBz | 2-CH$_2$CO$_2$H | (CH$_2$)$_3$ | HCC=CH. |
| 28 | 6 | H | H | p-ClBz | 2-CH$_2$CO$_2$H | (CH$_2$)$_3$ | HCC$_3$H$_5$ |
| 29 | 6 | H | H | p-ClBz | 4-CO$_2$H | (CH$_2$)$_3$ | HCH |
| 30 | 6 | H | H | C$_3$H$_5$ | 1-CH$_2$CO$_2$H | (CH$_2$)$_3$ | HCH |
| 31 | 6 | H | H | p-MeOBz | 1-CH$_2$CO$_2$H | (CH$_2$)$_3$ | HCH |
| 32 | 6 | H | H | o,p-Cl$_2$Bz | 1-CH$_2$CO$_2$H | (CH$_2$)$_3$ | HCH |
| 33 | 6 | H | H | m,p-Cl$_2$Bz | 1-CH$_2$CO$_2$H | (CH$_2$)$_3$ | HCH |
| 34 | 6 | H | H | p-MeSBz | 1-CH$_2$CO$_2$H | (CH$_2$)$_3$ | HCH |
| 35 | 6 | H | H | CH$_2$-c-C$_6$H$_{11}$ | 1-CH$_2$CO$_2$H | (CH$_2$)$_3$ | HCH |
| 36 | 6 | 6-CF$_3$ | 5-S(O)$_2$Me | 2-CH$_2$Th-4-Cl | 1-CH$_2$CO$_2$H | (CH$_2$)$_3$ | HCH |
| 37 | 6 | 7-N$_3$ | H | p-ClBz | 1-CH$_2$CO$_2$H | (CH$_2$)$_3$ | HCH |
| 38 | 6 | 8-CN | 7-F | (CH$_2$)$_2$-Ph-m-Ac | 2-CONHS(O)$_2$Me | (CH$_2$)$_3$ | HCH |
| 39 | 6 | 4-Me | 8-C(OH)Me$_2$ | p-CF$_3$SBz | 1-CH$_2$Tz | (CH$_2$)$_3$ | HCH |
| 40 | 6 | H | H | (CH$_2$)$_3$Ph | 1-CH$_2$CO$_2$H | (CH$_2$)$_3$ | HCH |
| 41 | 6 | H | H | Me | 1-CH$_2$CO$_2$H | (CH$_2$)$_3$ | HCH |
| 42 | 6 | H | H | p-MeS(O)Bz | 1-CH$_2$CO$_2$H | (CH$_2$)$_3$ | HCH |
| 43 | 7 | H | H | Me | 1-CH$_2$CO$_2$H | CHEtCH$_2$CH$_2$ | HCPh |
| 44 | 7 | H | H | Me | 1-CH$_2$CO$_2$H | (CH$_2$)$_3$ | HCH |
| 45* | 6 | H | H | p-ClBz | 1-CH$_2$CO$_2$H | (CH$_2$)$_3$ | HCH |
| 46* | 6 | H | H | p-ClBz | 1-CH$_2$CO$_2$H | (CH$_2$)$_3$ | HCH |

*Optical isomers of Example 1.

Conversion of the quinolinylmethoxy aniline derivative 8 to the hydrazine analogue 1a is effected through formation of the diazonium salt, followed by hydrazone formation with 3-methylpentane-2,4-dione to give hydrazone 24, and subsequent N-methylation using iodomethane under phase transfer conditions. The intermediate so obtained is then treated with hydrazine in hot ethanol to give hydrazine 1a.

Representative Compounds

Table I illustrates compounds representative of the present invention having the generic formula I$_b$. In the Other compounds of the invention are illustrated in Table II by Formula Ic.

TABLE II

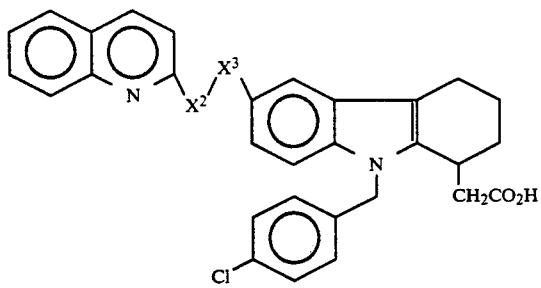

wherein the substituents are as follows:

| Ex. | $X^2-X^3$ |
|-----|-----------|
| 47  | $CH_2S$ |
| 48  | $CH_2S(O)_2$ |
| 49  | $CH=CH$ |
| 50  | $CH_2CH_2$ |

Assays for Determining Biological Activity

Two assays can be used to measure cytoprotective ability. These assays are; (A) an ethanol-induced lesion assay and (B) an indomethacin-induced ulcer assay and are described in EP 140,684.

Compounds of Formula I can be tested using the following assays to determine their mammalian leukotriene biosynthesis inhibiting activity.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15-24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/mL. A 500 µL aliquot of PMN suspension and test compound are preincubated for 2 minutes at 37°, followed by the addition of 10 µM A-23187. The suspension is stirred for an additional 4 minutes then bioassayed for $LTB_4$ content by adding an aliquot to a second 500 µL portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Human Polymorphonuclear (PMN) Leukocyte $LTB_4$ Assay

A. Preparation of Human PMN. Human blood was obtained by antecubital venepuncture from consenting volunteers who had not taken medication within the previous 7 days. The blood was immediately added to 10% (v/v) trisodium citrate (0.13M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16M) in Tris buffer (pH 7.65), and the PMNs resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4. Viability was assessed by Trypan blue exclusion and was typically greater than 98%.

(1) Boyum, A. Scand. J. Clin. Lab. Invest., 21 (Supp 97), 77 (1968).

B. Generation and Radioimmunoassay of $LTB_4$. PMNs (0.5 mL; $2.5 \times 10^5$ cells) were placed in plastic tubes and incubated (37° C., 2 min) with test compounds at the desired concentration or vehicle (DMSO, final concentration 0.2%) as control. The synthesis of $LTB_4$ was initiated by the addition of calcium ionophore A23187 (final concentration 10 µM) or vehicle in control samples and allowed to proceed for 5 minutes at 37° C. The reactions were then terminated by the addition of cold methanol (0.25 mL) and samples of the entire PMN reaction mixture were removed for radioimmunoassay of $LTB_4$.

Samples (50 µL) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-$LTB_4$ (10 nCi in 100 µL RIA buffer) and $LTB_4$-antiserum (100 µL of a 1:3000 dilution in RIA buffer) were added and the tubes vortexed. Reactants were allowed to equilibrate by incubation overnight at 4° C. To separate antibody-bound from free $LTB_4$, aliquots (50 µL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound $LTB_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al.[2] The amount of $LTB_4$ produced in test and control (approx. 20 ng/$10^6$ cells) samples were calculated. Inhibitory dose-response curves were constructed using a four-parameter algorithm and from these the $IC_{50}$ values were determined.

(2) Rokach, J.; Hayes, E. C.; Girard, Y.; Lombardo, D. L.; Maycock, A. L.; Rosenthal, A. S.; Young, R. N.; Zamboni, R.; Zweerink, H. J. Prostaglandins Leukotrienes and Medicine, 13, 21 (1984).

Asthmatic Rat Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No.

0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 μgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1–4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

The invention is further defined by reference to the following examples, which are intended to be illustrative and not limiting. All temperatures are in degrees Celsius.

EXAMPLE 1

9-Chlorobenzyl-6-(quinolin-2-ylmethoxy)-1,2,3,4-tetrahydrocarbazol-1-ylacetic acid Step 1

A mixture containing 2-(chloromethyl)quinoline hydrochloride (100.0 g), 4-acetamidophenol (70.69 g) and milled anhydrous $K_2CO_3$ (194 g) was stirred in DMF (1.2 L) using a mechanical stirrer for 48 hours. The mixture was carefully poured onto ice/water (3 L) with vigorous stirring. After the ice had melted, the solid was filtered and rinsed thoroughly with $H_2O$. It was recrystallized from 95% EtOH (ethanol) and filtered to give N-acetyl-4-(quinolin-2-ylmethoxy)aniline in three crops.

Step 2

A suspension of N-acetyl-4-(quinolin-2-ylmethoxy)aniline (Step 1, 108.9 g) in 1 L of 95% EtOH containing 10M KOH (120 mL) was heated at reflux under nitrogen in a heating mantle. When the hydrolysis was complete (approx. 36 h), the reaction mixture was cooled and EtOH was partially removed under vacuum. The mixture was then diluted with $H_2O$ (200 mL) and the fine off-white crystals were collected and thoroughly rinsed with water. The material, after air-drying, yielded 4-(quinolin-2-ylmethoxy)aniline which was used as such in the next step.

Step 3

A quantity of 84 g of 4-(quinolin-2-ylmethoxy)-aniline from Step 2 was suspended in 300 mL of deionized $H_2O$ and 84 mL of 12M HCl. The suspension was stirred vigourously to obtain a fine particle suspension. Then a precooled solution (5° C.) of 23.88 g of $NaNO_2$ dissolved in 75 mL of deionized $H_2O$ was added dropwise to the suspension at 5° C. over 25 minutes. The solution was stirred at 5° C. for 60 min to obtain the diazonium salt as a clear brown solution. The presence of excess $HNO_2$ was confirmed by KI-starch paper, and the pH of the solution was about 3.0. If a white suspension persisted after 1 h, the mixture was filtered through a glass wool plug, to give the diazonium salt in the filtrate.

In the meantime a sodium hydrosulfite ($Na_2S_2O_4$) solution was prepared by dissolving 321 g of $Na_2S_2O_4$ (approx. 85% purity) in 2 L of deionized $H_2O$, and cooled at 0° to 5° C. To this solution was added 15 mL of 2N NaOH and 2 L of $Et_2O$ (ether). The biphasic solution was kept near 0° C. by addition of crushed ice and was stirred vigorously. To this solution was added dropwise the diazonium salt solution with stirring maintained throughout. At the end of the addition an orange solid was formed and 600 mL of NaOH (2N) was added over 30 minutes. The reaction was finally stirred for 60 minutes at 25° C. The solid was collected, suspended in ether (1 L) and filtered. The process was repeated with 2 L of $H_2O$ to yield 4-(quinolin-2-ylmethoxy)- phenylhydrazine as a pale yellow solid after freeze-drying overnight; m.p. 73°–85° C. (dec).

Step 4

A quantity of 10 g of 4-(quinolin-2-ylmethoxy)-phenylhydrazine from Step 3 was added to a solution of 10.5 mL of diisopropylethylamine and 150 mL of $CH_2Cl_2$ (dichloromethane). To the yellow suspension was added 9.11 g of p-chlorobenzyl chloride followed by 3.64 g of $Bu_4NBr$ and 50 mL of $CH_2Cl_2$. The reaction was stirred for approximately 24 hours. When no starting material remained, the reaction was diluted with $H_2O$ and extracted 3 times with $CH_2Cl_2$. The combined organic phase was washed once with water and dried ($MgSO_4$), filtered and evaporated to dryness. The solid residue was dried under vacuum overnight prior to being swished in $Et_2O$/MeOH 90/10 to give 1-(p-chlorobenzyl)-1-[4-(quinolin-2-ylmethoxyl)-phenyl]-hydrazine as a pale yellow solid; m.p. 130° C.

Step 5

A solution of 886 mg of 1-(p-chlorobenzyl)-1-[4-(quinolin-2-ylmethoxy)phenyl]hydrazine from Step 4 in 1 ml of toluene was added to a suspension of 240 mg of sodium acetate (NaOAc) in 3 ml of acetic acid (HOAc); 440 mg of ethyl 2-oxocyclohexaneacetate was added and the suspension was stirred for 72 hours under nitrogen at room temperature. There was then added 5 ml of $H_2O$ and the organic phase was extracted with ethyl acetate (EtOAc). Chromatography on silica-gel using 30% EtOAc in hexane resulted in the isolation of 640 mg of the title compound as its ethyl ester.

Step 6

A solution of 550 mg of the ester from Step 5 in 3 ml of MeOH and 3 ml of tetrahydrofuran (THF) was treated with 1.5 ml of 2N NaOH solution for 16 hours, after which it was cooled to 0° and neutralized with 2.9 ml of 1N HCl. The reaction mixture was extracted with EtOAc (50 ml), the organic extract dried with $MgSO_4$ and evaporated to dryness to yield the title compound.

Calc: C, 72.86; H, 5.28; N, 5.48; Found: C, 72.78; H, 5.24; N, 5.44.

EXAMPLE 2

9-p-Chlorobenzyl-6-(quinolin-2-ylmethoxy)-1,2,3,4-tetrahydrocarbazol-2-ylacetic acid Using the method of Example 1 but using ethyl 3-oxocyclohexaneacetate in place of ethyl 2-oxocyclohexaneacetate, the title compound is prepared.

EXAMPLE 3

9-p-Chlorobenzyl-6-(quinolin-2-ylmethoxy)-1,2,3,4-tetrahydrocarbazol-2-ylcarboxylic acid Using the method of Example 1, but using ethyl 3-oxocyclohexane carboxylate as starting material, the title compound was prepared, after separation from a small amount of 9-p-chlorobenzyl-6-(quinolin-2-ylmethoxy)-1,2,3,4-tetrahydrocarbazol-4-ylcarboxylic acid; m.p. 236°–238° C. (dec.).

EXAMPLE 4

9-p-Chlorobenzyl-6-(quinolin-2-ylmethoxy)-1,2,3,4-tetrahydrocarbazol-1-ylcarboxylic acid Using the method of Example 1, but using ethyl 2-oxocyclohexane carboxylate as starting material, the title compound is prepared.

EXAMPLE 5

9-p-Chlorobenzyl-6-(quinolin-2-ylmethoxy)-1,2,3,4-tetrahydrocarbazol-3-ylcarboxylic acid Using the method of Example 1, but using ethyl 4-oxocyclohexane carboxylate as starting material, the title compound is prepared.

EXAMPLE 6

9-p-Chlorobenzyl-6-(quinolin-2-ylmethoxy)-1,2,3,4-tetrahydrocarbazol-1-ylpropanoic acid Using the method of Example 1 but using ethyl 2-oxocyclohexanepropanoate as starting material, the title compound was prepared; m.p. 163°–165° C.

EXAMPLE 7

9-p-Chlorobenzyl-6-(7-chloroquinolin-2-ylmethoxy)-1,2,3,4-tetrahydrocarbazol-1-ylacetic acid Using the method of Example 1, but using 1-(p-chlorobenzyl)-1-[4-(7-chloroquinolin-2-yl-methoxy)-phenyl]hydrazine as starting material, the title compound is prepared.

EXAMPLE 8

9-p-Chlorobenzoyl-6-(quinolin-2-ylmethoxy)-1,2,3,4-tetrahydrocarbazol-1-ylcarboxylic acid Step 1

To 350 mg of 4-(quinolin-2-ylmethoxy)phenylhydrazine (from Example 1, Step 3) in 1 ml of toluene is added a solution containing 300 mg of ethyl 2-oxocyclohexaneacetate dissolved in 3 ml of HOAc and 200 mg of NaOAc. The solution is allowed to stir under nitrogen for 72 hours, after which it is chromatographed on silica gel using 30% EtOAc in hexane, to yield ethyl 6-(quinolin-2-ylmethoxy)-1,2,3,4-tetrahydrocarbazol-1-ylcarboxylate.

Step 2

The product of the first step, (370 mg), dissolved in THF, is treated with 200 mg of p-chlorobenzoyl chloride, in the presence of 300 μL of triethylamine. After 24 hours, 5 ml H$_2$O is added and the product is extracted into EtOAc (15 ml ×3). Evaporation of the solvent leaves the title compound as its ethyl ester.

Step 3

The product of the second step is treated with one equivalent of NaOH under the conditions of Step 6 of Example 1 to provide the title compound.

EXAMPLE 9

9-p-Chlorobenzyl-6-(quinolin-2-ylmethoxy)-5-allyl-1,2,3,4-tetrahydrocarbazol-1-ylacetic acid Step 1

A mixture of 4-methoxyphenylhydrazine hydrochloride (50.0 mmol, 8.73 g) and ethyl 2-oxocyclohexaneacetate (50.0 mmol, 9.21 g) in absolute EtOH (25 ml) was heated at 85° C. for 1 h. After cooling to room temperature the mixture was filtered and the solvent was evaporated. Column chromatography (5% EtOAc in toluene) gave crystalline ethyl 6-methoxy-1,2,3,4-tetrahydrocarbazol-1-ylacetate (7.7 g, 53%).

Rf 0.50 (5% EtOAc in toluene).

$^1$H NMR (250 MHz, CDCl$_3$) δ8.65 brs, 1H), 7.19 (d, J=7.1 Hz, 1H), 6.93 (s, 1H), 6.78 (d, 1H), 4.23 (q, J=7.2 Hz, 2H), 3.86 (s, 3H), 3.42–3.25 (m, 1H), 2.78–2.54 (m, 4H), 2.15–1.55 (m, 4H), 1.30 (t, J=7.2 Hz, 3H).

Step 2

To a suspension of the ester from Step 1 (27.5 g, 95.7 mmol) in 1300 ml of CH$_2$Cl$_2$ at 0° C. was added anhydrous AlCl$_3$ (153 g, 1.15 mol) followed by ethanethiol (47.6 g, 766 mmol). The mixture was stirred for 2 hours at 0° C. and then poured onto an aqueous saturated solution of Rochelle salt. The layers were separated and the aqueous phase was extracted with CH$_2$Cl$_2$ (3×700 ml). Evaporation and flash chromatography (40% EtOAc in hexane) afforded 20.4 g (78%) of ethyl 6-hydroxy-1,2,3,4-tetrahydrocarbazol-1-ylacetate.

$^1$H NMR (250 MHz, CDCl$_3$) δ8.60 (br s, 1H), 7.13 (d, J=7.1 Hz, 1H), 6.93 (s, 1H), 6.78 (d, J=7.1 Hz, 1H), 5.63 (br s, 1H), 4.23 (q, J=7.2 Hz, 2H), 3.37 (m, 1H), 2.80–2.50 (m, 4H), 2.15–1.60 (m, 4H), 1.31 (t, J=7.2 Hz, 3H).

Step 3

The product from Step 2 (480 mg) is treated with 600 mg of allyl bromide dissolved in 2.0 ml of DMF to which has been added 250 mg of K$_2$CO$_3$. The reaction is stirred for 24 hours, after which H$_2$O is added. Extraction with diethyl ether (Et$_2$O), drying and evaporation of the ether phase yields ethyl 6-allyloxy-1,2,3,4-tetrahydrocarbazol-1-ylacetate.

Step 4

The product of Step 3 (400 mg) is heated in dichlorobenzene at 210° C. for 10 hours. Evaporation of the solvent and chromatography of the residue over silica gel using EtOAc-hexane yields ethyl 5-allyl-6-hydroxy-1,2,3,4-tetrahydrocarbazol-1-ylacetate.

Step 5

The compound from Step 4 (400 mg) is dissolved in 3.0 ml of DMF and 400 mg of 2-(chloromethyl)quinoline hydrochloride is added, followed by 275 mg of K$_2$CO$_3$. The reaction is stirred for 48 hours, 3.0 ml of H$_2$O is added and the product extracted into Et$_2$O. After washing with brine, the organic phase is dried and evaporated to yield ethyl 5-allyl-6-(quinolin-2-ylmethoxy)-1,2,3,4-tetrahydrocarbazol-1-ylacetate.

Step 6

To 454 mg (1 mmol) of ester from Step 5 in THF (15 ml) at −78° C. is added lithium hexamethyldisilazide in toluene (1.1 mmol), followed by hexamethylphosphoramide (1.5 ml). After 15 minutes, p-chlorobenzyl bromide (300 mg) is added and the reaction is allowed to warm to room temperature. The reaction mixture is then poured into 5% aqueous NH$_4$Cl, extracted with 2×100 ml Et$_2$O and the organic extracts dried over MgSO$_4$. Filtration and evaporation of the solvent left a crude residue, which, after chromatography over silica using EtOAc-hexane, yields ethyl 9-p-chlorobenzyl-6-(quinolin-2-ylmethoxy)-5-allyl-1,2,3,4-tetrahydrocarbazol-1-ylacetate.

Step 7

Hydrolysis of the product of Step 6 according to the method of Example 1, Step 6, yields the title compound.

EXAMPLE 10

9-p-Chlorobenzyl-6-(quinolin-2-ylmethoxy)-4-phenyl-1,2,3,4-tetrahydrocarbazol-1-ylacetic acid Step 1

A solution of 4-phenyl-2-oxo-3-cyclohexene-1-acetic acid (Tet. Lett. 1968, 4739) (10.0 g, 43.4 mmol) in Et$_2$O (150 ml) was treated with ethereal diazomethane at 0° C. until TLC indicated the reaction to be complete. The solvent was evaporated to yield methyl 4-phenyl-2-oxo-3-cyclohexene-1-acetate (10.6 g, quant.): Rf 0.33 (20% EtOAc in hexane);

$^1$H NMR (250 MHz) δ7.60–7.35 (m, 5H), 6.44 (s, 1H), 3.74 (s, 3H), 3.07–2.80 (m, 4H), 2.46–2.23 (m, 2H), 2.07–1.83 (m, 1H).

Step 2

A solution of the keto ester from Step 1 (5.20 g, 21.3 mmol) in EtOAc (150 ml) was hydrogenated over 10% Pd/C (520 mg) at 39 psi for 2.5 h. The mixture was filtered and the solvent was evaporated to give a clean oil. Flash chromatography (30% EtOAc in hexane) yielded 3.31 g (63%) of methyl 4-phenyl-2-oxocyclohexaneacetate as a mixture of diastereomers:

Rf 0.57 (30% EtOAc in hexane) two overlapping spots; $^1$H NMR (250 MHz) δ7.48–7.09 (m, 5H), 3.72 (s, 1.7H), 3.70 (s, 1.3H), 3.63 (m, 1H);

IR (film) 3030, 2950, 1735, 1720 cm$^{-1}$.

Step 3

A mixture of the ketone from Step 2 (316 mg, 1.28 mmol), the phenylhydrazine from Example 1 Step 4 (500 mg, 1.28 mmol), and NaOAc (116 mg, 1.41 mmol) was stirred in a mixed solvent of HOAc (1.1 ml) and toluene (20 ml) at R.T. for 24 hr.

The mixture was poured into saturated aqueous NH$_4$OAc (30 ml) and extracted with Et$_2$O (3×50 ml). The combined organic layers were washed with brine, dried over MgSO$_4$, and evaporated to dryness. Flash chromatography (30% EtOAc in hexane) afforded the corresponding crude hydrazones (470 mg). To the hydrazones was added PPE-dichloroethane (20 ml, 1:2) and the mixture was heated at 85° C. overnight. The cooled solution was poured into aqueous NH$_4$OAc and extracted with EtOAc. The combined organic layers were washed with brine, and dried over MgSO$_4$.

Evaporation of the solvent and chromatography afforded 57 mg of the methyl ester of the title compound.

Mass Spec. (CI, CH$_4$) m/z 601,603 (M+H)$^+$.

Step 4

To a solution of the ester from Step 3 (56 mg, 0.09 mmol) in THF (2.5 ml) was added H$_2$O (0.5 ml), MeOH (0.5 ml), and 1N LiOH (0.37 ml, 0.37 mmol). The mixture was stirred overnight, poured into saturated aqueous NH$_4$OAc and extracted with Et$_2$O. The combined organic layers were washed with brine, and dried over MgSO$_4$.

Evaporation of the solvent and crystallization from Et$_2$O/hexane afforded 18 mg of the title acid, mp 209°–210° C.

Mass Spec. (CI, CH$_4$) m/z 587,589 (M+H)$^+$.

EXAMPLE 11

9-Methyl-7-(quinolin-2-ylmethoxy)-4-phenyl-1,2,3,4-tetrahydrocarbazol-1-ylcarboxylic acid

EXAMPLE 12

9-Methyl-7-(quinolin-2-ylmethoxy)-4-p-chlorophenyl-1,2,3,4-tetrahydrocarbazol-1-ylacetic acid

EXAMPLE 13

9-Acetyl-7-(quinolin-2-ylmethoxy)-4-p-chlorophenyl-1,2,3,4-tetrahydrocarbazol-1-ylacetic acid

EXAMPLE 14

5-p-Chlorobenzyl-2-(quinolin-2-ylmethoxy)-10-p-chlorophenyl-5,6,7,8,9,10-hexahydrocyclohept[b]indole-6-acetic acid

EXAMPLE 15

5-p-Chlorobenzyl-2-(quinolin-2-ylmethoxy)-10-p-chlorophenyl-5,6,7,8,9,10-hexahydrocyclohept[b]indole-7-acetic acid

EXAMPLE 16

5-p-Chlorobenzyl-2-(quinolin-2-ylmethoxy)-10-p-chlorophenyl-5,6,7,8,9,10-hexahydrocyclohept[b]indole-7-carboxylic acid

EXAMPLE 17

5-Methyl-3-(quinolin-2-ylmethoxy)-10-p-chlorophenyl-5,6,7,8,9,10-hexahydrocyclohept[b]indole-6-acetic acid

EXAMPLE 18

5-Methyl-3-(quinolin-2-ylmethoxy)-10-p-chlorophenyl-5,6,7,8,9,10-hexahydrocyclohept[b]indole-7-carboxylic acid

EXAMPLE 19

5-Methyl-3-(quinolin-2-ylmethoxy)-10-p-chlorophenyl-5,6,7,8,9,10-hexahydrocyclohept[b]indole-7-carboxamide

EXAMPLE 20

9-p-Chlorobenzyl-6-(quinolin-2-ylmethoxy)-3-t-butyl-1,2,3,4-tetrahydrocarbazol-1-ylacetic acid Using the method of Example 1 but using ethyl 5-tert-butyl-2-oxocyclohexaneacetate in place of ethyl 2-oxocyclohexaneacetate, the title compound was prepared: C$_{35}$H$_{35}$ClN$_2$O$_3$•2H$_2$O.

Calc: C, 72.10; H, 6.60;, N, 4.79; Found: C, 72.37;, H, 6.36; N, 4.54

EXAMPLE 21

5-Methyl-9-p-methylsulfonylbenzyl-6-(quinolin-2-ylmethoxy)-4-oxo-1,2,3,4-tetrahydrocarbazol-1-ylacetic acid

EXAMPLE 22

9-p-Chlorobenzyl-6-(quinolin-2-ylmethoxy)-3-t-butyl-4-oxo-1,2,3,4-tetrahydrocarbazol-1-ylacetic acid

EXAMPLE 23

9-p-Chlorobenzyl-5-(quinolin-2-ylmethoxy)-1,2,3,4-tetrahydrocarbazol-1-ylacetic acid

EXAMPLE 24

9-Benzyl-6-(quinolin-2-ylmethoxy)-1,2,3,4-tetrahydrocarbazol-1-ylacetic acid

Step 1

To the phenol ester of Example 9, Step 2 (8.86 g, 32.4 mmol) in anhydrous DMF (50 ml) was added $K_2CO_3$ (6.72 g, 48.6 mmol) followed by 2-(chloromethyl)quinoline (7.49 g, 42.1 mmol). The mixture was stirred for 48 hours at room temperature. 2N HCl was added carefully until neutral to litmus paper. $H_2O$ (300 ml) was added and the mixture was extracted with EtOAc (6×100 ml). The combined organic layers were washed with water (400 ml) and dried over $MgSO_4$. Evaporation and flash chromatography (20% EtOAc in hexane) afforded ethyl 6-(quinolin-2-ylmethoxy)-1,2,3,4-tetrahydrocarbazol-1-ylacetate.

$^1$H-NMR (250 MHz, $CDCl_3$) δ8.67 (br s, 1H), 8.18 (d, J=8.4 Hz, 1H), 8.10 (d, J=8.5 Hz, 1H), 7.85–7.65 (3 overlapping d, 3H), 7.54 (t, J=7.32 Hz, 1H), 7.23 (t, J=8.07 Hz, 1H), 7.05 (s, 1H), 6.92 (d, J=8.7 Hz, 1H), 5.44 (s, 2H), 4.21 (q, 7.0 Hz, 2H), 3.40–3.20 (m, 1H), 2.65–2.50 (m, 4H), 2.10–1.50 (m, 4H), 1.29 (t, J=7.0 Hz, 3H).

Step 2

To a solution of ester from Step 1 (629 mg) in THF (15 ml) at −78° C. was added lithium hexamethyldisilazide (3.66 ml, 0.58M in toluene) followed by hexamethylphosphoramide (1.5 ml). After 20 minutes benzyl bromide (0.22 ml) was added and the mixture was allowed to warm to room temperature. The solution was poured into aq. $NH_4OAc$ and extracted with $Et_2O$ (3×50 ml). The combined organic layers were washed with brine and dried over $MgSO_4$. Evaporation of the solvent and crystallization ($Et_2O$) afforded 438 g. of ethyl 9-benzyl-6-(quinolin-2-ylmethoxy)-1,2,3,4-tetrahydrocarbazol-1-ylacetate.

Step 3

370 mg of ester from Step 2 in THF (7 ml), MeOH (1.75 ml), and $H_2O$ (1.75 ml) was treated with LiOH (2.9 ml, 1.0M), and stirred at room temperature for 24 hours. The mixture was diluted with water and neutralized with HCl (1N). The resulting precipitate was filtered, washed with water and cold $Et_2O$ to afford 305 mg of the title compound. m.p. 183° C. decomp.

EXAMPLE 25

4-p-Chlorobenzyl-7-(quinolin-2-ylmethoxy)-1,2,3,4-tetrahydrocyclopent[b]indole-3-acetic acid

EXAMPLE 26

4-Methyl-6-(quinolin-2-ylmethoxy)-1-phenyl-1,2,3,4-tetrahydrocyclopent[b]indole-3-acetic acid

EXAMPLE 27

9-p-Chlorobenzyl-6-(quinolin-2-ylmethoxy)-4-ethynyl-1,2,3,4-tetrahydrocarbazol-2-ylacetic acid

EXAMPLE 28

9-p-Chlorobenzyl-6-(quinolin-2-ylmethoxy)-4-allyl-1,2,3,4-tetrahydrocarbazol-2-ylacetic acid

EXAMPLE 29

9-p-Chlorobenzyl-6-(quinolin-2-ylmethoxy)-1,2,3,4-tetrahydrocarbazol-4-ylcarboxylic acid

EXAMPLE 30

9-Allyl-6-(quinolin-2-ylmethoxy)-1,2,3,4-tetrahydrocarbazol-1-ylacetic acid

Following the method of Example 24, but using allyl bromide instead of benzyl bromide (Step 2), the title compound was prepared; m.p. 150° C.

EXAMPLE 31

9-p-Methoxybenzyl-6-(quinolin-2-ylmethoxy)-1,2,3,4-tetrahydrocarbazol-1-ylacetic acid Following the method of Example 24, but using p-methoxybenzyl bromide instead of benzyl bromide (Step 2), the title compound was prepared; m.p. 194° C. decomp.

EXAMPLE 32

9-o,p-Dichlorobenzyl-6-(quinolin-2-ylmethoxy)-1,2,3,4-tetrahydrocarbazol-1-ylacetic acid Following the method of Example 24, but using 2,4-dichlorobenzyl chloride instead of benzyl bromide (Step 2), the title compound was obtained; m.p. 210° C. decomp.

EXAMPLE 33

9-m,p-Dichlorobenzyl-6-(quinolin-2-ylmethoxy)-1,2,3,4-tetrahydrocarbazol-1-ylacetic acid Following the method of Example 24, but using 3,4-dichlorobenzyl chloride instead of benzyl bromide (Step 2), the title compound was obtained; m.p. 203° C. decomp.

EXAMPLE 34

9-p-Methylthiobenzyl-6-(quinolin-2-ylmethoxy)-1,2,3,4-tetrahydrocarbazol-1-ylacetic acid Following the method of Example 24, but using p-methylthiobenzyl chloride instead of benzyl bromide (Step 2), the title compound was obtained; m.p. 204° C.

EXAMPLE 35

9-Cyclohexylmethyl-6-(quinolin-2-ylmethoxy)-1,2,3,4-tetrahydrocarbazol-1-ylacetic acid Following the method of Example 24, but using cyclohexylmethyl bromide instead of benzyl bromide (Step 2), the title compound was obtained; m.p. 115° C. decomp.

EXAMPLE 36

9-(4-Chlorothien-2-ylmethyl)-5-methylsulfonyl-6-(6-trifluoromethylquinolin-2-ylmethoxy)-1,2,3,4-tetrahydrocarbazol-1-ylacetic acid

EXAMPLE 37

6-7-Azidoquinolin-2-ylmethoxy-9-p-chlorobenzyl-1,2,3,4-tetrahydrocarbazol-1-ylacetic acid

EXAMPLE 38

9-(2-(3-Acetylphenyl)ethyl)-6-(8-cyanoquinolin-2-ylmethoxy)-7-fluoro-1,2,3,4-tetrahydrocarbazol-1-ylacetic acid

EXAMPLE 39

6-(4-Methylquinolin-2-ylmethoxy)1-tetrazol-5-ylmethyl)-9-(p-trifluoromethylthio)benzyl-1,2,3,4-tetrahydrocarbazole-8-(a,a-dimethyl)methanol

EXAMPLE 40

9-(3-Phenylpropyl)-6-(quinolin-2-ylmethoxy)-1,2,3,4-tetrahydrocarbazol-1-ylacetic acid Following the method of Example 24, but using 1-bromo-3-phenylpropane instead of benzyl bromide (Step 2), the title compound was obtained.

| $C_{33}H_{31}N_2O_3 \cdot Na \cdot H_2O$ | C | H | N |
|---|---|---|---|
| Calculated | 72.78 | 6.11 | 5.14 |
| Found | 72.22 | 6.01 | 5.21 |

EXAMPLE 41

9-Methyl-6-(quinolin-2-ylmethoxy)-1,2,3,4-tetrahydrocarbazol-1-ylacetic acid

Following the method of Example 24, but using iodomethane instead of benzyl bromide (Step 2), the title compound was obtained.

| $C_{25}H_{23}N_2O_3 \cdot Na \cdot 1.5H_2O$ | C | H | N |
|---|---|---|---|
| Calculated | 66.80 | 5.83 | 6.23 |
| Found | 66.30 | 5.34 | 6.26 |

EXAMPLE 42

9-p-Methylsulfinylbenzyl-6-(quinolin-2-ylmethoxy)-1,2,3,4-tetrahydrocarbazol-1-ylacetic acid Step 1:

To 354 mg of 9p-methylthiobenzyl-6-(quinolin-2-ylmethoxy)-1,2,3,4-tetrahydrocarbazol-1-ylacetic acid ethyl ester from Example 34, Step 2, in 5 ml $CH_2Cl_2$ at 0° C. was added 190 mg of m-chloroperbenzoic acid. The resulting mixture was stirred for 1 hour at 0° C. The reaction mixture was diluted with $Et_2O$ and washed consecutively with a solution of $NaHCO_3$, water and brine. The crude product obtained after evaporation of the organic layer was purified on silica gel by flash chromatography eluting with 5% MeOH in $CH_2Cl_2$ and yielded 275 mg of the pure sulfoxide derivative.

Step 2

Following the procedure of Example 24, Step 3, the title compound was obtained; m.p. 135° C. decomp.

EXAMPLE 43

1-Ethyl-9-methyl-7-(quinolin-2-ylmethoxy)-4-phenyl-1,2,3,4-tetrahydrocarbazol-1-ylacetic acid A mixture of 1-(3-(quinolin-2-ylmethoxy)phenyl)-1-methylhydrazine prepared according to Scheme 6 (540) mg, 1.93 mmol), NaOAc (173 mg, 2.11 mmol), HOAc (2.21 ml, 38.6 mmol), and 2-carbomethoxymethyl-2-ethyl-5-phenylcyclohexanone (U.S. Pat. No. 4,578,298) (482 mg, 1.76 mmol) in toluene (10 ml) was stirred at room temperature for 3 days. The mixture was poured into sat. aq. $NH_4OAc$ and extracted with $Et_2O$ (3×50 ml). The combined organic layers were washed with brine, dried over $MgSO_4$ and evaporated to dryness. The residue was taken up in dichloroethane (1.5 ml) and treated with dichloroethane/polyphosphoric ester (1:1, 310 μl). After 2 hours at 85° C. the mixture was cooled, poured into sat. aq. $NH_4OAc$ and extracted with EtOAc. Flash chromatography on silica gel afforded 80 mg of the methyl ester of the title compound.

To a solution of the above indole ester (69 mg, 0.13 mmol) in THF (4 ml) and MeOH (1 ml) was added LiOH (IN, 0.4 ml, 0.40 mmol). The mixture was stirred at r.t. for 19 hours. An additional 0.2 ml LiOH was added, the solution was stirred at 60° C. for 4.5 hours and at r.t. for 15 hours. The mixture was neutralized with 1N HCl, $H_2O$ was added, and the solution was extracted with EtOAc. Evaporation of the solvent and chromatography on silica gel afforded the title acid, m.p. 185°–191° C.

What is claimed is:

1. A compound of the formula:

wherein:

each of $R^1$, $R^2$, $R^3$, $R^4$ and $R^{10}$ is independently hydrogen, halogen, lower alkyl, lower alkenyl, lower alkynyl, $-CF_3$, $-CN$, $-NO_2$, $-N_3$, $-C(OH)R^6R^6$, $-C(O)OR^{12}$, $-SR^{13}$, $-S(O)R^{13}$, $-S(O)_2R^{13}$, $-S(O)_2NR^{15}R^{15}$, $-C(O)NR^{15}R^{15}$, $-OR^{15}$, $-NR^{15}R^{15}$, $-C(O)R^{16}$ or $-(CH_2)_rR^{21}$;

$R^5$ is hydrogen or $X-R^9$, $R^6$ is independently hydrogen or lower alkyl;

$R^7$ is $-(CR^6R^6)_sQ$ and replaces one of the $R^6$ groups attached to the carbons with make up ring A;

$R^8$ is hydrogen, $R^9$, $-CR^{23}=CR^{24}R^{25}$, $-C(Cl)=CCl_2$ or $R^6$ plus $R^8$ on the same carbon atom may be a double bonded oxygen (=O);

$R^9$ is alkyl, alkenyl, or $-(CH_2)_tPh(R^{10})_2$;

$R^{12}$ is hydrogen, lower alkyl or $-CH_2R^{21}$;

$R^{13}$ is $-CF_3$ or $R^{14}$;

$R^{14}$ is lower alkyl or $-(CH_2)_uR^{21}$;

$R^{15}$ is hydrogen, $-C(O)R^{16}$, or $R^{14}$;

$R^{16}$ is hydrogen, lower alkenyl, lower alkynyl, or $R^{13}$;

$R^{17}$ is $-(CH_2)_v-C(R^{18}R^{18})-(CH_2)_v-R^{19}$ or $-CH_2-C(O)NR^{15}R^{15}$;

$R^{18}$ is hydrogen or lower alkyl;

$R^{20}$ contains up to 21 carbon atoms and is (1) a hydrocarbon radical or (2) an acyl radical of an organic, acyclic or monocyclic carboxylic acid;

$R^{21}$ is phenyl substituted with 1 or 2 $R^{22}$ groups;

$R^{22}$ is hydrogen, halogen, lower alkyl, lower alkoxy, lower alkylthio, lower alkylsulfonyl, lower alkylcarbonyl, $-CF_3$, $-CN$, $-NO_2$ or $-N_3$;

$R^{23}$ is $R^{18}$ or $R^{23}$ and $R^{24}$ may form a bond;

$R^{24}$ is $R^6$ or $R^{23}$ and $R^{24}$ may form a bond;

$R^{25}$ is $R^6$;

p is 2 to 5;

q is 0 or 1;

p+q is 3 to 5;

r is 0 to 2;

s is 0 to 4;

t is 0 to 3;

u is 0 to 3;

v is 0 to 3;

W is O, S or $NR^{15}$;

X is C(O), CR⁶R⁶, S(O)₂ or a bond;
X²—X³ is CH₂O, CH₂S, CH₂S(O)₂, CH₂CH₂, or CH=CH;
Q is —C(O)OR¹², —C(O)NHS(O)₂R¹³, —NHS(O)₂R¹³, —S(O)₂NHR¹⁵, —C(O)NR¹⁵R¹⁵, —C(O)OR¹⁷ or CH₂OH;
or the pharmaceutically acceptable salts thereof.

2. A compound of claim 1 wherein:
each of R¹, R², R³ and R⁴ is hydrogen;
R⁵ is X—R⁹;

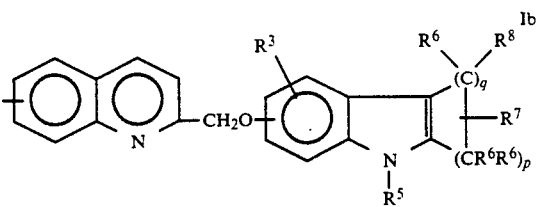

TABLE

| | Attach point | R¹ | R³ | R⁵ | R⁷ | (CR⁶R⁶)ₚ | (R⁶CR⁸)q |
|---|---|---|---|---|---|---|---|
| 1 | 6 | H | H | p-ClBz | 1-CH₂CO₂H | (CH₂)₃ | HCH |
| 2 | 6 | H | H | p-ClBz | 2-CH₂CO₂H | (CH₂)₃ | HCH |
| 3 | 6 | H | H | p-ClBz | 2-CO₂H | (CH₂)₃ | HCH |
| 4 | 6 | H | H | p-ClBz | 1-CO₂H | (CH₂)₃ | HCH |
| 5 | 6 | H | H | p-ClBz | 3-CO₂H | (CH₂)₃ | HCH |
| 6 | 6 | H | H | p-ClBz | 1-(CH₂)₂CO₂H | (CH₂)₃ | HCH |
| 7 | 6 | 7-Cl | H | p-ClBz | 1-CH₂CO₂H | (CH₂)₃ | HCH |
| 8 | 6 | H | H | p-ClPhCO | 1-CH₂CO₂H | (CH₂)₃ | HCH |
| 9 | 6 | H | 5-C₃H₅ | p-ClBz | 1-CH₂CO₂H | (CH₂)₃ | HCH |
| 10 | 6 | H | H | p-ClBz | 1-CH₂CO₂H | (CH₂)₃ | HCPH |
| 11 | 7 | H | H | Me | 1-CH₂CO₂H | (CH₂)₃ | HCPh |
| 12 | 7 | H | H | Me | 1-CH₂CO₂H | (CH₂)₃ | MeC-p-ClPh |
| 13 | 7 | H | H | COMe | 1-CH₂CO₂H | (CH₂)₃ | HC-p-ClPh |
| 14 | 2 | H | H | p-ClBz | 6-CH₂CO₂H | (CH₂)₄ | HC-p-ClPh |
| 15 | 2 | H | H | p-ClBz | 7-CH₂CO₂H | (CH₂)₄ | HC-p-ClPh |
| 16 | 2 | H | H | p-ClBz | 7-CO₂H | (CH₂)₄ | HCH |
| 17 | 3 | H | H | Me | 6-CH₂CO₂H | (CH₂)₄ | HC-p-ClPh |
| 18 | 3 | H | H | Me | 7-CO₂H | (CH₂)₄ | HC-p-ClPh |
| 19 | 3 | H | H | Me | 7-CONH₂ | (CH₂)₄ | HC-p-ClPh |
| 20 | 6 | H | H | p-ClBz | 1-CH₂CO₂H | CH₂CH₂CH(t-Bu) | HCH |
| 21 | 6 | H | 5-Me | p-MeS(O)₂Bz | 1-CH₂CO₂H | (CH₂)₃ | C=O |
| 22 | 6 | H | H | p-ClBz | 1-CH₂CO₂H | CH₂CH(t-Bu)CH₂ | C=O |
| 23 | 5 | H | H | p-ClBz | 1-CH₂CO₂H | (CH₂)₃ | HCH |
| 24 | 6 | H | H | Bz | 1-CH₂CO₂H | (CH₂)₃ | HCH |
| 25 | 7 | H | H | p-ClBz | 3-CH₂CO₂H | (CH₂)₂ | HCH |
| 26 | 6 | H | H | Me | 3-CH₂CO₂H | (CH₂)₂ | HCPh |
| 27 | 6 | H | H | p-ClBz | 2-CH₂CO₂H | (CH₂)₃ | HCC=CH |
| 28 | 6 | H | H | p-ClBz | 2-CH₂CO₂H | (CH₂)₃ | HCC₃H₅ |
| 29 | 6 | H | H | p-ClBz | 4-CO₂H | (CH₂)₃ | HCH |
| 30 | 6 | H | H | C₃H₅ | 1-CH₂CO₂H | (CH₂)₃ | HCH |
| 31 | 6 | H | H | p-MeOBz | 1-CH₂CO₂H | (CH₂)₃ | HCH |
| 32 | 6 | H | H | o,p-Cl₂Bz | 1-CH₂CO₂H | (CH₂)₃ | HCH |
| 33 | 6 | H | H | m,p-Cl₂Bz | 1-CH₂CO₂H | (CH₂)₃ | HCH |
| 34 | 6 | H | H | p-MeSBz | 1-CH₂CO₂H | (CH₂)₃ | HCH |
| 35 | 6 | H | H | CH₂-c-C₆H₁₁ | 1-CH₂CO₂H | (CH₂)₃ | HCH |
| 37 | 6 | 7-N₃ | H | p-ClBz | 1-CH₂CO₂H | (CH₂)₃ | HCH |
| 38 | 6 | 8-CN | 7-F | (CH₂)₂-Ph-m,-Ac | 2-CONHS(O)₂Me | (CH₂)₃ | HCH |
| 39 | 6 | 4-Me | 8-C(OH)Me₂ | p-CF₃SBz | 1-CH₂Tz | (CH₂)₃ | HCH |
| 41 | 6 | H | H | Me | 1-CH₂CO₂H | (CH₂)₃ | HCH |
| 42 | 6 | H | H | p-MeS(O)Bz | 1-CH₂CO₂H | (CH₂)₃ | HCH |
| 43 | 7 | H | H | Me | 1-CH₂CO₂H | CHEtCH₂CH₂ | HCPh |
| 44 | 7 | H | H | Me | 1-CH₂CO₂H | (CH₂)₃ | HCH |

R⁸ is R⁹;
R¹⁰ is hydrogen or halogen;
the CH₂O is attached to the 2-position of the quinoline ring;
p+q is 4;
X is a bond;
X²—X³ is CH₂O;
Q is —C(O)OR¹²;
or the pharmaceutically acceptable salts thereof.

3. A compound of claim 1 of formula Ib wherein the substituents are as follows:

4. A compound of claim 1 of Formula Ic

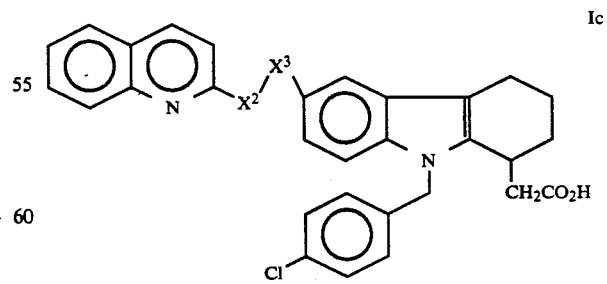

wherein the substituents are as follows:

| | X²-X³ |
|---|---|
| 47 | CH₂S |

-continued

| | $X^2-X^3$ |
|---|---|
| 48 | $CH_2S(O)_2$ |
| 49 | CH=CH |
| 50 | $CH_2CH_2$ |

5. The following compounds of claim 1:
9-p-Chlorobenzyl-6-(quinolin-2-ylmethoxy)-1,2,3,4-tetrahydrocarbazol-1-ylacetic acid;
9-p-Chlorobenzyl-6-(quinolin-2-ylmethoxy)-1,2,3,4-tetrahydrocarbazol-2-ylacetic acid;
9-p-Chlorobenzyl-6-(quinolin-2-ylmethoxy)-1,2,3,4-tetrahydrocarbazol-2-ylcarboxylic acid;
9-p-Chlorobenzyl-6-(quinolin-2-ylmethoxy)-1,2,3,4-tetrahydrocarbazol-1-ylcarboxylic acid;
9-p-Chlorobenzyl-6-(quinolin-2-ylmethoxy)-1,2,3,4-tetrahydrocarbazol-3-ylcarboxylic acid;
9-p-Chlorobenzyl-6-(quinolin-2-ylmethoxy)-1,2,3,4-tetrahydrocarbazol-1-ylpropanoic acid;
9-p-Chlorobenzyl-6-(7-chloroquinolin-2-ylmethoxy)-1,2,3,4-tetrahydrocarbazol-1-ylacetic acid;
9-p-Chlorobenzoyl-6-(quinolin-2-ylmethoxy)-1,2,3,4-tetrahydrocarbazol-1-ylcarboxylic acid;
9-p-Chlorobenzyl-6-(quinolin-2-ylmethoxy)-5-allyl-1,2,3,4-tetrahydrocarbazol-1-ylacetic acid;
9-p-Chlorobenzyl-6-(quinolin-2-ylmethoxy)-4-phenyl-1,2,3,4-tetrahydrocarbazol-1-ylacetic acid;
9-Methyl-7-(quinolin-2-ylmethoxy)-4-phenyl-1,2,3,4-tetrahydrocarbazol-1-ylcarboxylic acid;
9-Methyl-7-(quinolin-2-ylmethoxy)-4-p-chlorophenyl-1,2,3,4-tetrahydrocarbazol-1-ylacetic acid;
9-Acetyl-7-(quinolin-2-ylmethoxy)-4-p-chlorophenyl-1,2,3,4-tetrahydrocarbazol-1-ylacetic acid;
5-p-Chlorobenzyl-2-(quinolin-2-ylmethoxy)-10-p-chloro-phenyl-5,6,7,8,9,10-hexahydrocyclohept[b]indole-6-acetic acid;
5-p-Chlorobenzyl-2-(quinolin-2-ylmethoxy)-10-p-chloro-phenyl-5,6,7,8,9,10-hexahydrocyclohept[b]indole-7-acetic acid;
5-p-Chlorobenzyl-2-(quinolin-2-ylmethoxy)-10-p-chloro-phenyl-5,6,7,8,9,10-hexahydrocyclohept[b]indole-7-carboxylic acid;
5-Methyl-3-(quinolin-2-ylmethoxy)-10-p-chlorophenyl-5,6,7,8,9,10-hexahydrocyclohep[b]indole-6-acetic acid;
5-Methyl-3-(quinolin-2-ylmethoxy)-10-p-chlorophenyl-5,6,7,8,9,10-hexahydrocyclohept[b]indole-7-carboxylic acid;
5-Methyl-3-(quinolin-2-ylmethoxy)-10-p-chlorophenyl-5,6,7,8,9,10-hexahydrocyclohept[b]indole-7-carboxamide;
9-p-Chlorobenzyl-6-(quinolin-2-ylmethoxy)-3-t-butyl-1,2,3,4-tetrahydrocarbazol-1-ylacetic acid;
5-Methyl-9-p-methylsulfonylbenzyl-6-(quinolin-2-ylmethoxy)-4-oxo-1,2,3,4-tetrahydrocarbazol-1-ylacetic acid;
9-p-Chlorobenzyl-6-(quinolin-2-ylmethoxy)-3-t-butyl-4-oxo-1,2,3,4-tetrahydrocarbazol-1-ylacetic acid;
9-p-Chlorobenzyl-5-(quinolin-2-ylmethoxy)-1,2,3,4-tetrahydrocarbazol-1-ylacetic acid;
9-p-Benzyl-5-(quinolin-2-ylmethoxy)-1,2,3,4-tetrahydrocarbazol-1-ylacetic acid;
4-p-Chlorobenzyl-7-(quinolin-2-ylmethoxy)-1,2,3,4-tetrahydrocyclopent[b]indole-3-acetic acid;
4-Methyl-6-(quinolin-2-ylmethoxy)-1-phenyl-1,2,3,4-tetrahydrocyclopent[b]indole-3-acetic acid;
9-p-Chlorobenzyl-6-(quinolin-2-ylmethoxy)-4-ethynyl-1,2,3,4-tetrahydrocarbazol-2-ylacetic acid;
9-p-Chlorobenzyl-6-(quinolin-2-ylmethoxy)-4-allyl-1,2,3,4-tetrahydrocarbazol-2-ylacetic acid;
9-p-Chlorobenzyl-6-(quinolin-2-ylmethoxy)-1,2,3,4-tetrahydrocarbazol-4-ylcarboxylic acid;
9-Allyl-6-(quinolin-2-ylmethoxy)-1,2,3,4-tetrahydrocarbazol-1-ylcarboxylic acid;
9-p-Methoxybenzyl-6-(quinolin-2-ylmethoxy)-1,2,3,4-tetrahydrocarbazol-1-ylacetic acid;
9-o,p-Dichlorobenzyl-6-(quinolin-2-ylmethoxy)-1,2,3,4-tetrahydrocarbazol-1-ylacetic acid;
9-m,p-Dichlorobenzyl-6-(quinolin-2-ylmethoxy)-1,2,3,4-tetrahydrocarbazol-1-ylacetic acid;
9-p-Methylthiobenzyl-6-(quinolin-2-ylmethoxy)-1,2,3,4-tetrahydrocarbazol-1-ylacetic acid;
9-Cyclohexylmethyl-6-(quinolin-2-ylmethoxy)-1,2,3,4-tetrahydrocarbazol-1-ylacetic acid;
7-Azidoquinolin-2-ylmethoxy-9-p-chlorobenzyl-1,2,3,4-tetrahydrocarbazol-1-ylacetate acid;
9-(2-(3-Acetylphenyl)ethyl)-6-(8-cyanoquinolin-2-ylmethoxy)-7-fluoro-1,2,3,4-tetrahydrocarbazol-1-ylacetic acid;
9-(3-Phenylpropyl)-6-(quinolin-2-ylmethoxy)-1,2,3,4-tetrahydrocarbazol-1-ylacetic acid;
9-Methyl-6-(quinolin-2-ylmethoxy)-1,2,3,4-tetrahydrocarbazol-1-ylacetic acid; and
9-p-Methylsulfinylbenzyl-6-(quinolin-2-ylmethoxy)-1,2,3,4-tetrahydrocarbazol-1-ylacetic acid.

6. A pharmaceutical composition comprising a therapeutically effective amount of a compound of claim 1 and a pharmaceutically acceptable carrier.

7. A method of preventing the synthesis, the action, or the release of SRS-A or leukotrienes in a mammal which comprises administering to said mammal an effective amount of a compound of claim 1.

8. The method of claim 7 wherein the mammal is man.

9. A compound of claim 3 in optically active form which is 9-p-chlorobenzyl-6-(quinolin-2-ylmethoxy)-1,2,3,4-tetrahydrocarbzaol-1-ylacetic acid.

* * * * *